United States Patent [19]
Michael

[11] Patent Number: 5,996,963
[45] Date of Patent: Dec. 7, 1999

[54] DENTAL CASTING MOLD DEVICE

[75] Inventor: Robert M. Michael, Westampton, N.J.

[73] Assignee: Ceramco Inc., Burlington, N.J.

[21] Appl. No.: 09/012,162

[22] Filed: Jan. 22, 1998

Related U.S. Application Data

[60] Provisional application No. 60/038,733, Feb. 14, 1997.

[51] Int. Cl.$^6$ .................................................. B29C 39/00
[52] U.S. Cl. ........................... 249/54; 249/53 R; 433/34; 433/213
[58] Field of Search ..................... 249/53 R, 54, 249/97; 425/175; 433/34, 72, 73, 74, 75, 213; 264/16, 17, 18, 19, 20

[56] References Cited

U.S. PATENT DOCUMENTS

| | | | |
|---|---|---|---|
| Re. 35,263 | 6/1996 | Silva et al. ................................. | 433/74 |
| 2,367,767 | 1/1945 | Gale ........................................... | 18/55.1 |
| 2,700,219 | 1/1955 | Lindley ....................................... | 32/32 |
| 2,786,272 | 3/1957 | Lindley ....................................... | 32/32 |
| 3,495,333 | 2/1970 | Kuhn .......................................... | 32/32 |
| 3,702,027 | 11/1972 | Marshall et al. ............................. | 32/11 |
| 3,704,519 | 12/1972 | Lystager ..................................... | 32/11 |
| 3,838,187 | 9/1974 | Thomas ..................................... | 264/17 |
| 3,937,773 | 2/1976 | Huffman .................................... | 264/17 |
| 4,059,902 | 11/1977 | Shiokawa .................................. | 32/12 |
| 4,078,310 | 3/1978 | Horger, Jr. ................................. | 32/12 |
| 4,122,606 | 10/1978 | Roman ...................................... | 32/11 |
| 4,203,219 | 5/1980 | Wiener ...................................... | 433/74 |
| 4,265,619 | 5/1981 | Lucki et al. ................................. | 433/54 |
| 4,283,173 | 8/1981 | Browne et al. ............................. | 433/34 |
| 4,299,574 | 11/1981 | Neihart ...................................... | 433/213 |
| 4,300,884 | 11/1981 | Camacho .................................. | 433/74 |
| 4,319,875 | 3/1982 | Beckwith .................................. | 433/60 |
| 4,368,042 | 1/1983 | Felstead et al. ........................... | 433/213 |
| 4,398,884 | 8/1983 | Huffman .................................... | 433/74 |
| 4,403,961 | 9/1983 | Gurney ..................................... | 433/213 |
| 4,439,151 | 3/1984 | Whelan ..................................... | 433/60 |
| 4,494,934 | 1/1985 | Huffman .................................... | 433/213 |
| 4,508,506 | 4/1985 | Jackson .................................... | 433/74 |
| 4,538,987 | 9/1985 | Weissman ................................. | 433/60 |
| 4,548,581 | 10/1985 | Huffman .................................... | 433/64 |
| 4,689,013 | 8/1987 | Lustig ........................................ | 433/181 |
| 4,708,648 | 11/1987 | Weissman ................................. | 433/49 |
| 4,721,464 | 1/1988 | Roden et al. .............................. | 433/74 |
| 4,767,330 | 8/1988 | Burger ....................................... | 433/74 |
| 4,767,331 | 8/1988 | Hoe ........................................... | 433/213 |
| 4,842,242 | 6/1989 | Huffman .................................... | 249/54 |
| 4,854,825 | 8/1989 | Bez et al. ................................... | 417/265 |
| 4,898,359 | 2/1990 | Gopon ....................................... | 249/54 |

(List continued on next page.)

FOREIGN PATENT DOCUMENTS

| | | |
|---|---|---|
| 0 629 385 | 12/1994 | European Pat. Off. . |
| 2 590 475 | 5/1987 | France . |
| 35 40 122 | 5/1987 | Germany . |
| 90/08513 | 8/1990 | WIPO . |

OTHER PUBLICATIONS

Official Gaszzette, Erratum, Aug. 9, 1994.
Nu Logic, The E–Z Tray Model System, 5 pages.
VIDENT, KO Model System, 4 pages.

*Primary Examiner*—Kuang Y. Lin
*Attorney, Agent, or Firm*—Douglas J. Hura; James B. Bieber

[57] ABSTRACT

A dental stone casting mold device (10) for use with a hardenable stone material (21) includes associated first and second side walls (11, 12) first and second end walls (13, 14) and a floor (15), forming an open top cavity (16). Each first and second side walls (11, 12) and first and second end walls (13, 14) extend from the floor (15) in a lateral direction, such that each has a portion (17) proximate to the floor (15) and a portion (18) distal thereto. There is also at least one slot (22) in the floor (15) removably receiving a stone retaining spine (20). In a preferred embodiment, each of first and second side wall (11, 12) carries a plurality of spaced indexing ribs (60). In another embodiment, each distal end 18 of the first and second side walls (11, 12) have integrally associated lateral extensions or webs (80) therefrom. Device (10) may also be provided with indexing bar or articulator attachment structures (101, 110).

20 Claims, 7 Drawing Sheets

U.S. PATENT DOCUMENTS

| | | | |
|---|---|---|---|
| 4,917,347 | 4/1990 | Fenick | 249/54 |
| 4,943,237 | 7/1990 | Bryan | 433/213 |
| 4,957,435 | 9/1990 | Jinoian et al. | 433/34 |
| 4,997,370 | 3/1991 | Mayclin | 433/74 |
| 5,076,786 | 12/1991 | Callne | 433/60 |
| 5,100,317 | 3/1992 | Darnand | 433/60 |
| 5,129,822 | 7/1992 | Dobbs | 433/34 |
| 5,197,874 | 3/1993 | Silva et al. | 433/74 |
| 5,221,203 | 6/1993 | Callne | 433/58 |
| 5,306,145 | 4/1994 | Michael | 433/34 |
| 5,328,366 | 7/1994 | Callne | 433/34 |
| 5,360,337 | 11/1994 | Westdyk | 433/64 |
| 5,393,227 | 2/1995 | Nooning | 433/74 |
| 5,466,152 | 11/1995 | Walter | 433/60 |
| 5,506,095 | 4/1996 | Callne | 433/34 |

DENTAL CASTING MOLD DEVICE

This application claims the benefit of U.S. Provisional application Ser. No. 60/038,733 filed Feb. 14, 1997.

TECHNICAL FIELD

The present invention relates to a mold device for use in preparing a dental stone cast model. More particularly, the invention relates to such a device having a removable retaining spine affixed thereto such that dental stone material can be poured into the tray, such that the material physically engages and is retained by the retaining spine. Furthermore, the invention relates to such a device having indexing ribs within the interior of the mold device, a structure for removable affixing an articulator, and structure for facilitating the removal and replacement of a cast model into the tray.

BACKGROUND OF THE INVENTION

In the field of dental care, replacement teeth are typically retained in place by means of bridge work or the like extending from the replacement tooth and anchored to adjacent healthy teeth. The manufacture of such replacement teeth and their mechanical bridge structure requires careful work to insure proper fitting thereof with respect to adjacent teeth. Also, restoration procedures such as the capping of decayed or broken teeth likewise requires precise positioning with respect to approximate teeth.

To accurately form and position the replacement tooth or cap, a dentist usually makes a dental go negative or impression of the relevant tooth or gap typically including at least the adjacent teeth. This impression may be partial, unilateral or bilateral, depending upon the extent of the work to be done, and serves as a mold for eventual developing of a die of the patient's tooth to be replaced or restored.

For example, when a tooth is to be crowned or otherwise rebuilt, it is conventional to make a negative, casting or impression of the tooth using a rubber-like impression material. The impression then used as a mold for preparing a positive replica of the tooth to be restored. The replica is then used to assist in forming a crown model of the tooth which in turn provides a form or die for making the crown. If needed, a full-bite positive replica of the teeth will be prepared for use in insuring that the upper and lower teeth sets will be closed together properly.

During preparation of the replica tooth or cap, it is usually necessary to remove the casting of its precusor or mock-up from the complete casting, often several times. To do this, the casting, such as for example, a jaw-shaped positive or replica of the gum and upper or lower teeth set is cut through and a slice of replica gum and teeth set removed from the set. In this regard, in order to provide a template on which to reassemble the pieces of the set, a removable base is typically affixed, such as for example, by casting onto the replica teeth set and gum before it is cut into sections. In order that the individual pieces may be accurately reassembled in the initial mold, and in accordance with heretofore conventional practices, each piece is provided with a locating pin or the like which fits into a hole in the base. The pins are set into the replica pieces during the molding operation.

This technique for preparing the replica such that it can be reassembled in a mold or on a base in proper relation to adjacent teeth in the set requires that the pins be very accurately positioned in the fluid dental stone in which the replica tooth or teeth are to be formed. This procedure is difficult because the mold is filled with the molding material thus obscuring the pins. Further, the outline of the teeth is not visible from the outside of the mold.

One solution to these drawbacks is described in U.S. Pat. No. 5,306,145. This patent describes a molding device having an open-top cavity for containing dental stone material, and a spine removably insertable into the floor of the cavity. While this device overcame many of the heretofore known drawbacks to modeling devices, a need still exists for a modeling device which will allow very precise control over the placement of the tooth model into and out of the cavity repeatedly.

Furthermore, a need also exists for a tray with improved set stone removable capability, without detrimentally effecting the accuracy of the replacement of the stone into the tray. The tray should also be capable of efficiently cooperating with an articulator device.

OBJECTS OF THE INVENTION

It is therefore, an object of the present invention to provide a dental stone casting mold device.

It is a further object of the present invention to provide a device as above, that will allow precise indexing of individual sections of a stone cast model.

It is another object of the invention to provide a device as above configured to permit efficient removal of the set stone cast model and accurate replacement of the model into the device.

It is still an other object of the invention to provide a device as above configured to cooperatively interact with an articulator device.

These and other objects of the present invention which will become apparent from the specification and claims to follow, are carried out by the invention as hereinafter described and claimed.

SUMMARY OF THE INVENTION

In general, embodiments of the present invention include a dental stone casting mold device for use with a hardenable stone material. Certain of the embodiments comprise associated first and second side wall means, first and second end wall means and floor means forming an open top cavity means. Each of the first and second side wall means and the first and second end wall means extend from the floor means in a lateral direction, such that each has a portion proximate to floor means and a portion distal thereto. The inventive device also comprises a slot means in the floor means for removably receiving a stone retaining spine means, and the first and second side wall means are in a spaced and opposing relation to each other.

In certain embodiments, each of the first and second side wall means carries a plurality of spaced indexing ribs extending in a direction substantially parallel to the lateral direction extension of its associated side wall, such that each indexing rib has a linear dimension. At least one indexing rib of the first side wall has a linear dimension greater than the linear dimension of at least one indexing rib of the second side wall.

In another embodiment of the invention, each distal end of the first and second side walls have integrally associated lateral extensions therefrom.

In still another embodiment, each distal end of the first and second wall means has a linearly extending, raised fracture lip.

In a further embodiment of the invention, the first end wall means carries an integrally associated articulator attachment means; such that a pair of the dental stone casting mold devices can be removably positioned in a parallel, spaced, opposing relation by attachment of the articulator through the articulator attachment means.

In yet a further embodiment of the invention, the slot means comprises at least a first slot aperture and a second slot aperture, and the spine means comprises at least a first slot retaining portion and a second slot retaining portion. The first slot retaining portion is removably receivable within the first slot aperture, and the second slot retaining portion is receivable within the second slot aperture.

PREFERRED EMBODIMENTS OF THE INVENTION

A device for use in the preparation of a dental stone cast or a positive replica of a patient's teeth, is generally indicated by the number 10 on the attached drawings. For the sake of this discussion, device 10 will hereinafter be referred to as tray 10. Tray 10 is used in the preparation of dental models by techniques that are conventional other than for those techniques making use of the novel and unique characteristics of tray 10 to be hereinafter described. Such conventional modeling techniques as were briefly discussed above, are described for example, in U.S. Pat. No. 5,306,145 which is hereby incorporated by reference for such disclosure.

Figure 3:
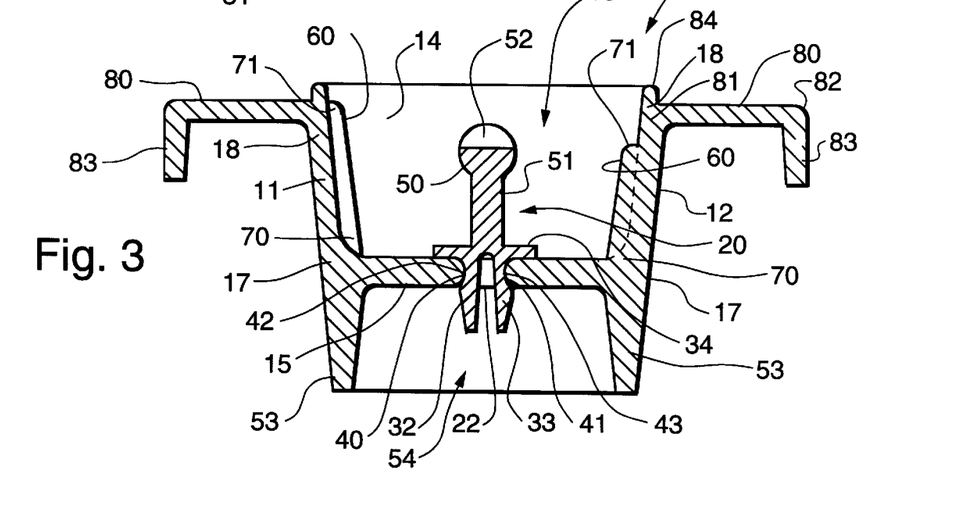
FIG. 3 is a side elevation and sectional view of the dental modeling tray according to the invention, and taken along lines 3—3 of FIG. 1.

Tray 10 includes associated first and second side wall means 11 and 12 respectively, first and second end wall means 13 and 14 respectively, and floor means 15, together cooperating to form an open top cavity 16. As will be more fully discussed below, tray 10 is preferably used in combination with a spine member 20. When affixed to tray 10, spine member 20 and tray lo cooperate to form a dental modeling device to accept and removably retain a dental stone modeling material. A dental stone material model is shown by way of example as material 21 in FIG. 7. Each first and second side wall 11 and 12 and first and second end walls 13 and 14 extend from floor 15 in a lateral direction, such that each has a portion 17 proximate to floor 15 and a portion 18 distal thereto (FIG. 3).

Tray 10 as depicted in the drawings and as described herein, is rectangular in shape only for the sake of this discussion. It will be appreciated that other shapes including nonlinear portions and the like may also be useful and which are within the scope of the invention. Thus, a full arch tray 10 or any portion thereof is within the scope of the invention.

Figure 1:
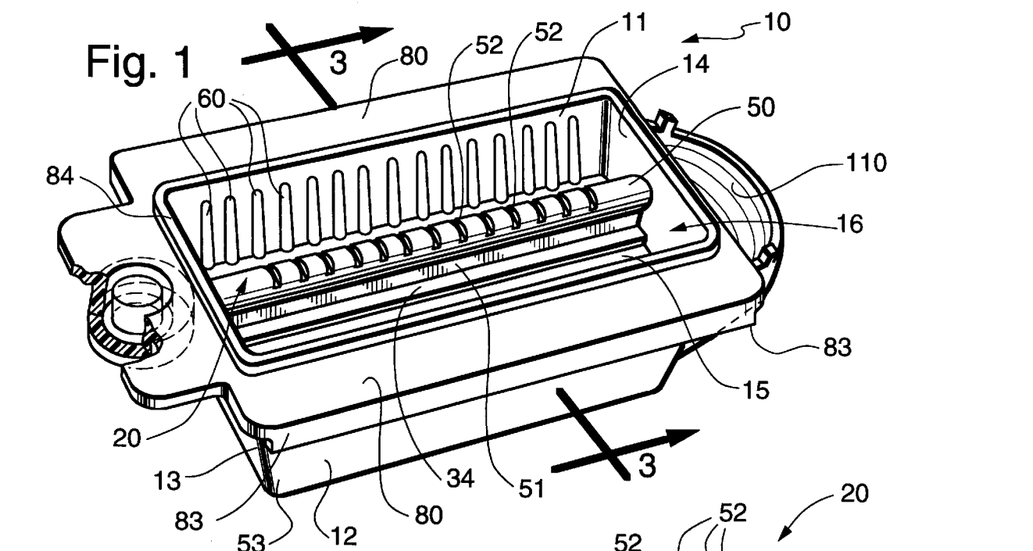
FIG. 1 is a perspective view of one embodiment of a dental modeling tray having a spine member received therein, according to the concepts of the present invention.
Figure 2:
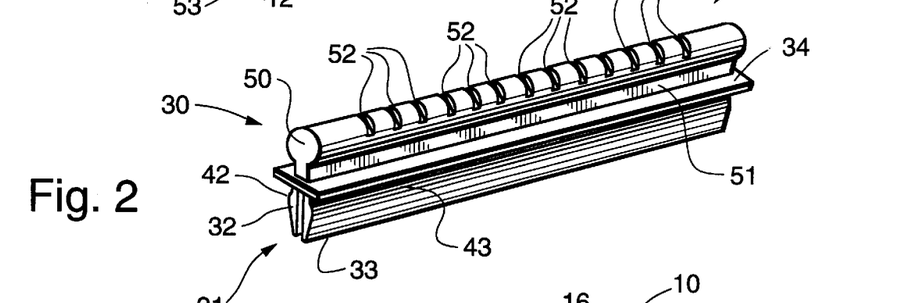
FIG. 2 is a perspective view of one embodiment of the spine member of FIG. 1.

A preferred embodiment of tray 10 includes a through slot 22 in floor 15. Slot 22 is preferably positioned in a central portion of floor 15 and extends in a linear direction substantially parallel to sides 11 and 12. Spine 20 includes a stone material retaining portion generally designated by the number 30 and a slot retaining portion 31 (FIG. 2).

Slot retaining portion 31 includes resilient and opposing retention member 32 and 33, configured to be cooperatively and removably received within and through slot 22, such that the retention member means 32 and 33 are deformable when received within slot 22 and resiliently expandable after passage through slot 22, to removably retain spine 20 and hence, any attached stone material, within tray 10.

Spine 20 is also provided with a flange 34 positioned between slot retaining portion 31 and stone material retaining portion 30, such that flange 34 limits the distance to which the retention members 32 and 33 can be received through slot 22. That is, flange 34 will physically engage or be seated upon floor 15. Inner edges 40 and 41 of slot 22 may be configured to cooperatively, physically engage complementary indentations 42 and 43 of spine 22 when flange 34 is seated upon floor 15.

Figure 10:
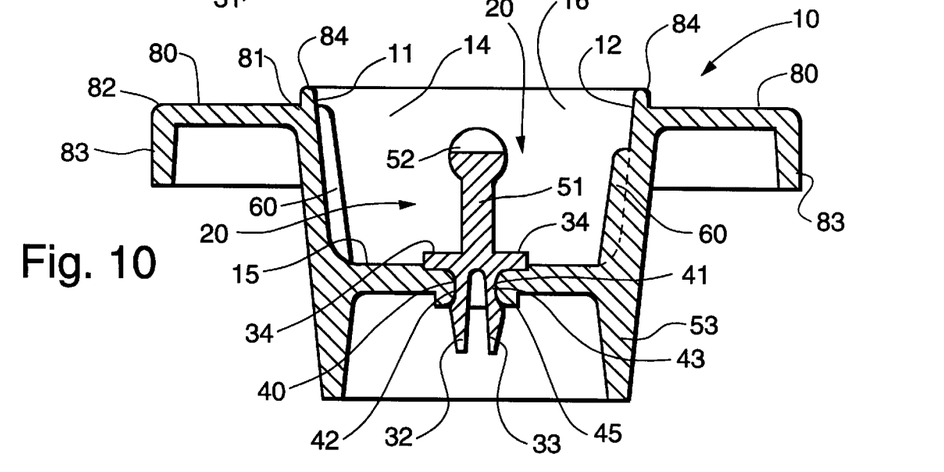
FIG. 10 is a side elevation and sectional view of the dental modeling tray according to the invention, and taken along lines 10—10 of FIG. 8.
Figure 11:
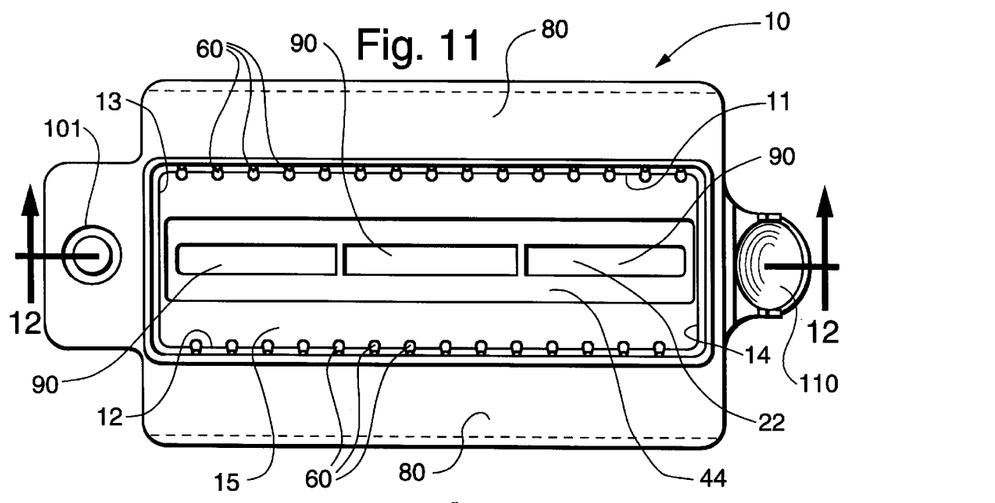
FIG. 11 is a top plan view of the dental modeling tray of FIG. 8, shown without the spine member.
Figure 12:
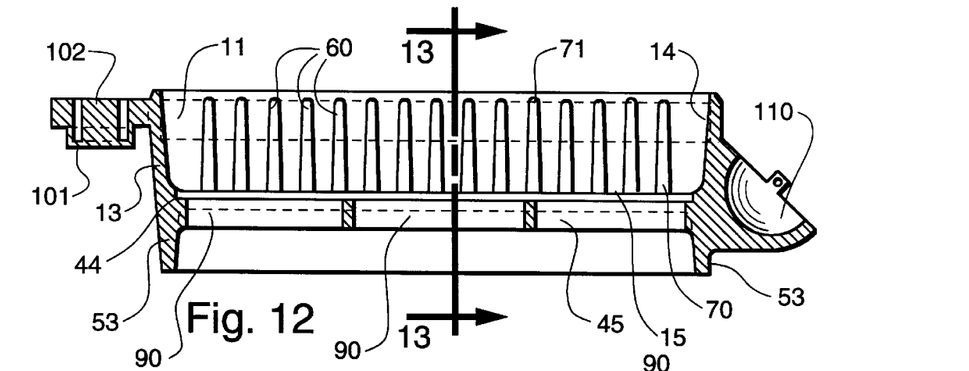
FIG. 12 is a side, plan view taken along lines 12—12 of FIG. 11.
Figure 13:
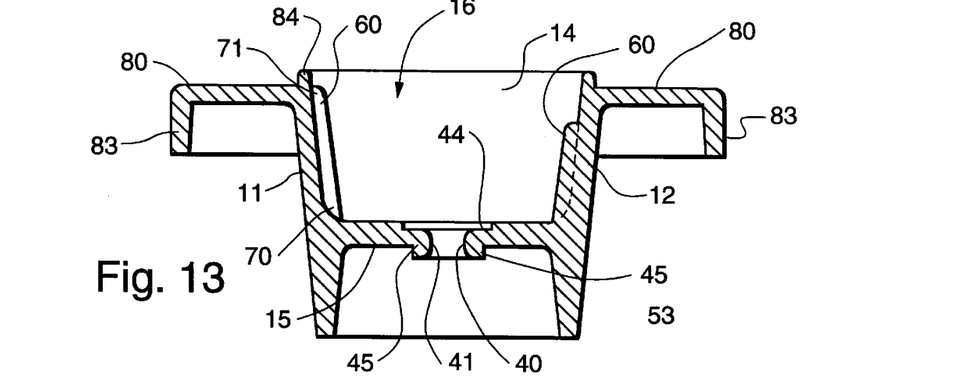
FIG. 13 is an end, plan view taken along lines 13—13 of FIG. 12.

As shown in FIGS. 10–13, an alternative and preferred embodiment of tray 10 includes a groove 44 in floor 15 proximate to or more preferably straddling slot 22. Flange 34 is received within groove 44 (FIG. 10) and is thereby more precisely positioned within tray 10. Further, slot 22 in another embodiment, also depicted in FIG. 13, may terminate on an underside of floor 15, that is the portion of floor 15 facing away from open cavity 16, in a guidewall 45. As shown in FIG. 10, guidewall 45 is preferably positioned on both sides of slot 22, and serves to guide retention members 32 and 33 through slot 22 and to provide a larger surface area (as compared to the embodiment depicted in FIG. 3) for complementary inner edges 40 and 41 and indentations 42 and 43. This provides a more secure "lock up" or retention of spine 20 within tray 10. As shown in the drawings, retention members 32 and 33 may be tapered to facilitate entry into slot 22 and the deforming thereof.

Stone material retaining portion 30 includes a linearly extending bead 50 supported by a neck 51. It will be appreciated that when wet stone material is poured into tray 10, in any manner such as by the one described in U.S. Pat. No. 5,306,145, it will flow around bead 50. When set, the stone material will be mechanically retained in that position by physical contact with bead SO and neck S1. That is, bead 50 will be imbedded within set stone material 21. Neck 51 may be of any length and the length will vary depending upon the desires of the user and the requirements of the particular application. All such lengths are within the scope of the invention.

Further, while a preferred configuration of bead 50 is depicted in the drawings as being bulbous in cross section, any shape is within the scope of the invention. Bead 50 may also be provided with a plurality of retaining grooves 52 to provide for secure mechanical physical interaction with the stone material 21, and to substantially limit or even prevent lateral movement of stone material 21 hardened about bead 50.

Tray 10 is provided with a downwardly extending skirt 53 extending laterally from floor 15 in a direction opposite than that of first and second side wall means 11 and 12, such that an open bottom cavity 54 is formed opposite that of open top cavity 16. Skirt 53 thereby provides a base for tray 10 and allows room for retention members 32 and 33 to protrude slot 22 and still allow tray 10 to be placed upon and supported by a flat surface (not shown).

First and second side walls 11 and 12 are placed in a spaced and opposing relation to each other. Each of the first and second side walls 11 preferably carry a plurality of spaced indexing ribs 60. Indexing ribs 60 extend in a direction substantially parallel to the lateral direction extension of its associated side wall 11, 12, such that each indexing rib 60 has a linear dimension. In the embodiment of the invention as depicted in the drawings, at least one indexing rib 60 of first side wall 11 has a linear dimension greater than the linear dimension of at least one indexing rib 60 carried by second side wall 12. Thus, when the hardened stone material 21 is removed from tray 10 affixed to spine 20, and subsequently cut into individual portions, the portions can be replaced into tray 10 in the exact same location as before being removed because the indexing ribs 60 guide the replacement.

Further, by being of different linear dimensions, the individual model portions cannot be replaced backwards. The ribs 60 will create complementary grooves (not shown) in the set stone material and thus, the shorter grooves in the set stone material 21 will not be fully seatable in a longer rib 60. Other similar configurations, including alternating dimensions or even ribs all having the same dimension (neither of which are shown) are all within the scope of the invention.

Figure 4:
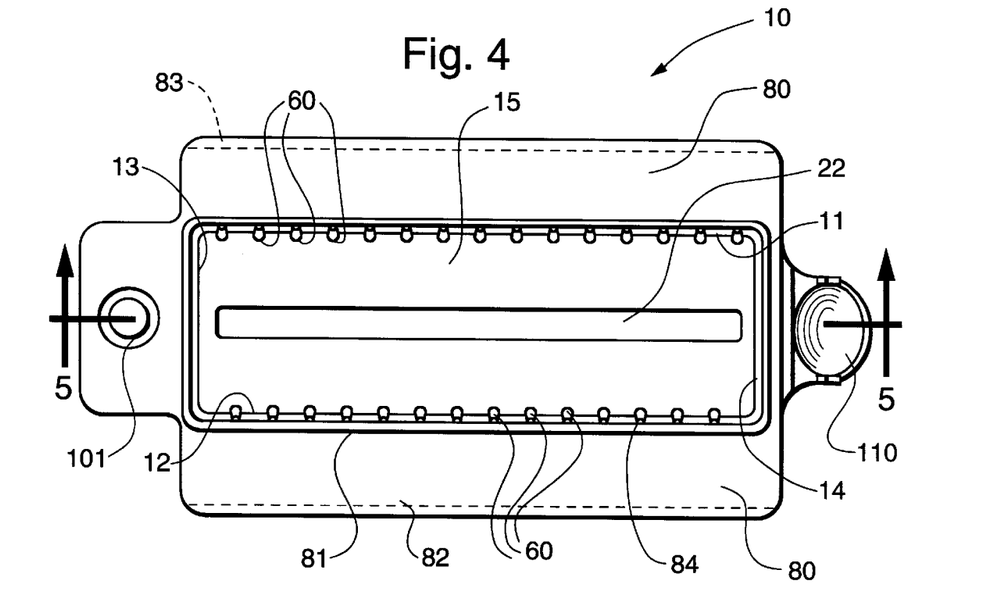
FIG. 4 is a top plan view of the dental modeling tray of FIG. 1, shown without the spine member.
Figure 5:
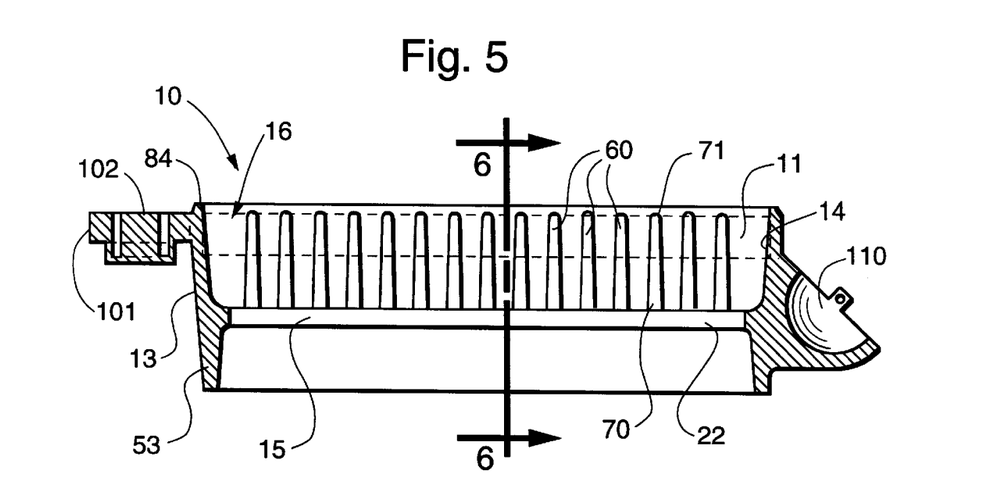
FIG. 5 is a side, plan view taken along lines 5—5 of FIG. 4.
Figure 6:
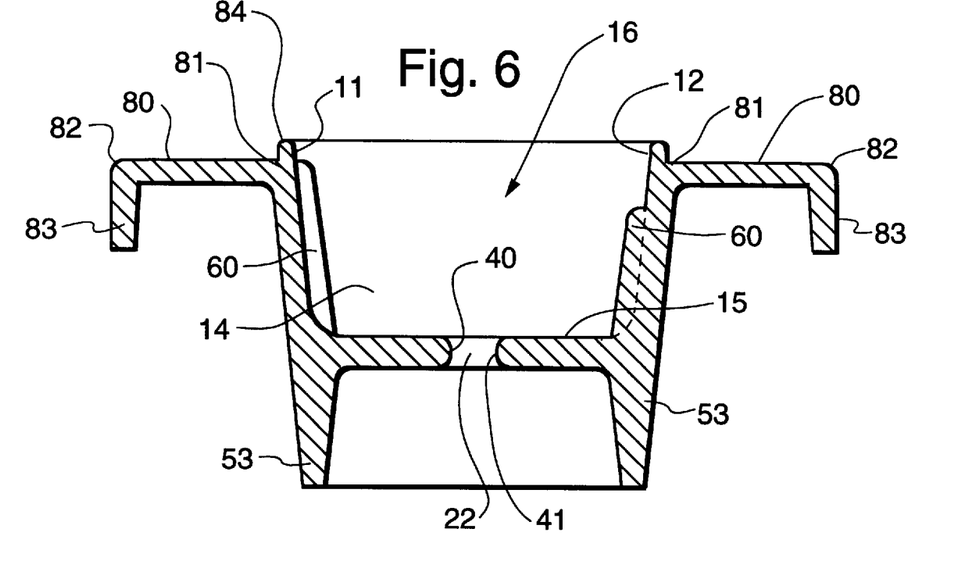
FIG. 6 is an end, plan view taken along lines 6—6 of FIG. 5.

As best shown in FIG. 4, each of the plurality ribs 60 of first sidewall 11 are positioned in a staggered opposing relation to the plurality of indexing ribs 60 of the second side wall 12. That is, each rib 60 of one sidewall 11, 12 does not directly oppose a rib 60 of the opposite sidewall 11, 12, but rather is offset therefrom. This also promotes the proper removal and seating of stone sections into and out of tray 10. Indexing ribs 60 preferably have a portion 70 proximate to floor 15 and a portion 71 distal thereto. Indexing ribs 60 taper outwardly from distal portion 70 to proximate portion 71.

Each distal portion 18 of first and second side walls 11 and 12 terminate in an integrally formed and associated lateral web 80. Web 80 generally defines the top of tray 10, and may have any desired dimension lateral from walls 11–14. Web 80 serves to provide a handhold for the user of tray 10 and also to provide a shield against stone material 21 from overflowing to the underneath of tray 10. As will be appreciated by those skilled in the art, removal of stone material from a modeling tray requires that the stone be disengageable from tray 10. Any mechanical interaction between stone material and tray profiles will make this difficult. Web 80 helps prevent physical and mechanical interaction with any such profile, and also allows the user to easily clean away any excess wet stone material 21.

Further, web 80 can also be positioned to laterally extend from both first and second sidewalls 11, 12, as shown, such that a user can grasp web 80 on either side of tray 10 and exert force thereon to bend sidewalls 11 and 12 away from each other, thereby further facilitating removal of stone material 21 from tray 10. Sidewall 11 and 12 proximate portions 17 are closer to each other than are the respective distal portions 18 of opposing sidewalls 11 and 12 (FIG. 3). That is, sidewalls 11 and 12 taper upwardly and outwardly toward open top cavity 16, also promoting efficient removal and replacement of stone material 21 into and out of tray 10.

At least one laterally extending web 80 from first or second sidewall 11 or 12 has a portion 81 proximate to its associated sidewall 11, 12 and a portion 82 distal thereto. The distal portion 82 may terminate in a linearly extending lip) 83. Lip 83 also facilitates shielding and the user grasping tray 10 to bend distal portions 18 of sidewalls 11, 12 away from each other. To even more fully allow such resilient bending or flexing of tray 10, tray 10 is preferably fabricated from a material such as high density polyethylene or other material to allow flexing.

Distal portions 18 of one or all walls 11–14 may also terminate in a linearly extending, raised fracture lip 84. A knife or other edge (not shown) may be slipped underneath stone material 21 and on top of web 80 to engage fracture lip 84. Stone material 21 may thereby be broken from efficiently removed from tray 10.

Figure 9:
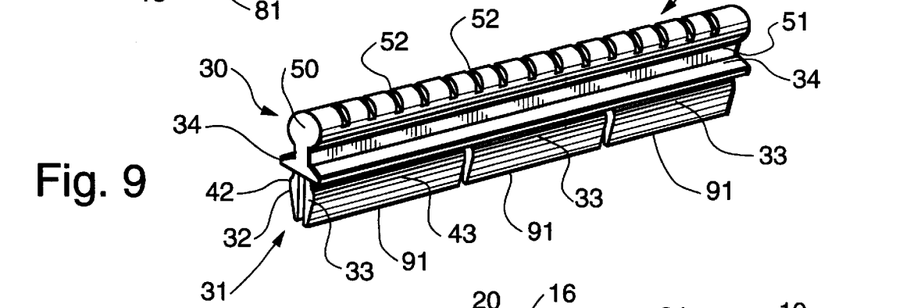
FIG. 9 is a perspective view of another embodiment of a spine member as in FIG. 8.

In an alternative embodiment of the invention, as is best depicted in FIGS. 8–13, tray 10 is provided with a plurality of slots 22. For sake of discussion, this slot 22 includes a plurality of slot apertures 90. The embodiment depicted in the drawings has three slot apertures 90, although any number are within the scope of the invention. Spine 20 is complementary configured to have a plurality of retaining portion sections 91 (FIG. 9). Each retaining portion section 91 is receivable within a complementary slot aperture 90, and is otherwise substantially similar to retaining portion 31 as discussed hereinabove. It is preferred to arrange a plurality of slot apertures 90 in a juxtaposed, linear relation, as is shown.

Tray 10 may be provided with a vertical stop pin 100 (FIG. 7) affixed to a retaining sleeve 101. In this way, two trays 10 may be affixed in an opposing, spaced relation. Retaining sleeve 101 may be formed by any means, such as by fabricating tray 10 with removable plug 102. In use, plug 102 is removed from tray 10 thereby forming open sleeve 101 into which stop pin 100 may be inserted. Preferably, stop pin 100 is adhesively bonded at the desired location.

Figure 7:
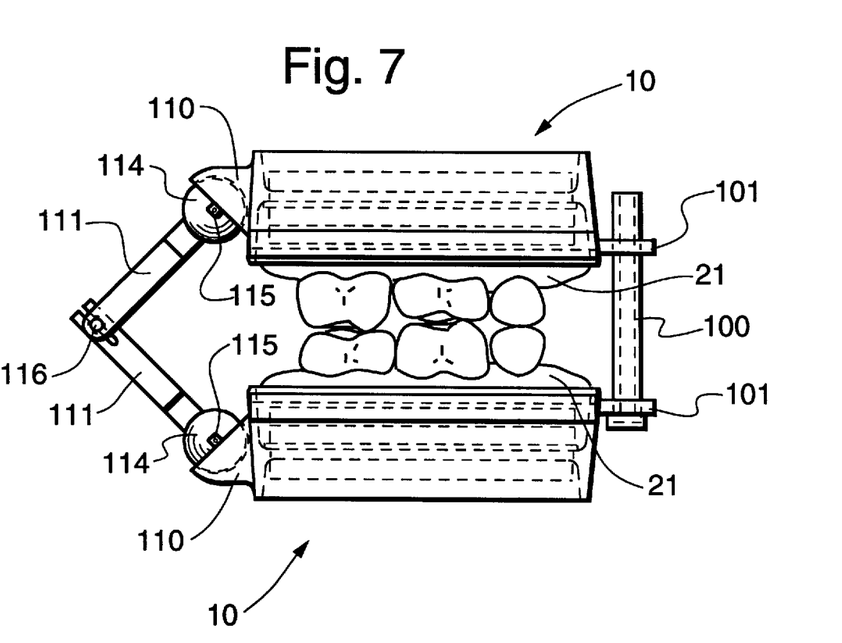
FIG. 7 is a side plan view of two dental modeling trays as in FIG. 1, shown for environmental purposes as positioned in a spaced opposing relationship by an articulator and an indexing bar, and having dental models within each of the modeling trays.
Figure 8:
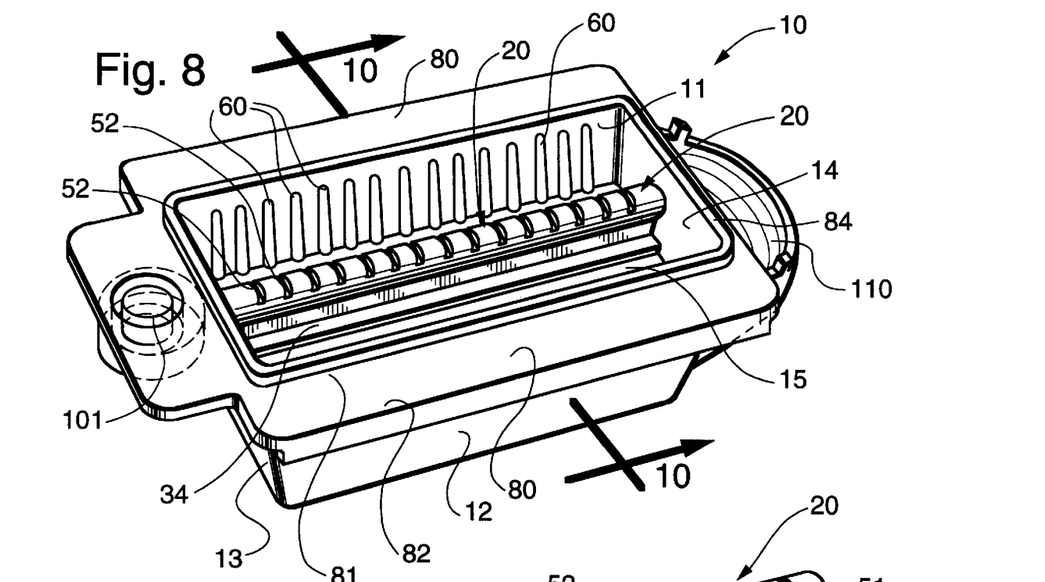
FIG. 8 is a perspective view of an alternative embodiment of a modeling tray according to the present invention.

Alternatively, tray 10 may be provided with an articulator attachment means, such as socket 110. Any articulator attachment method and structure is within the scope of the invention and will vary depending upon among other things, the articulator design. An example of an articulator useful with socket 110 is that discussed in U.S. Pat. No. 4,548,581 which is hereby incorporated by reference for such disclosure. Articulator 111 has first and second arms 112 and 113 respectively, which each terminate in a ball 114. Each ball 114 is receivable in a socket 110, perhaps positioned by retaining fingers 115, to cooperatively form a ball and socket joint. Articulator arms 112 and 113 are hinged at hinge member 116. Two trays 10 may thereby be articulated respective to each other to correctly align two stone models 21.

Figure 14:
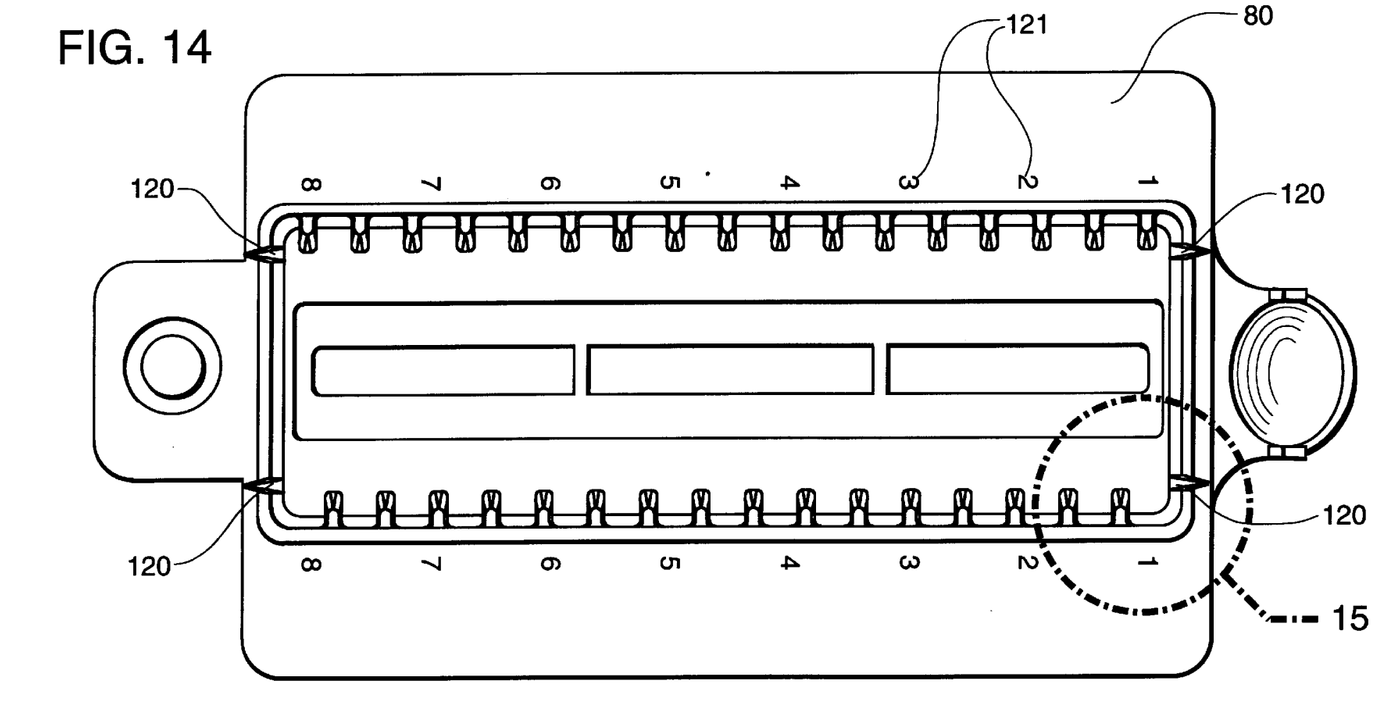
FIG. 14 is an alternative embodiment of the tray in FIG. 11, and is a top plan view.
Figure 15:
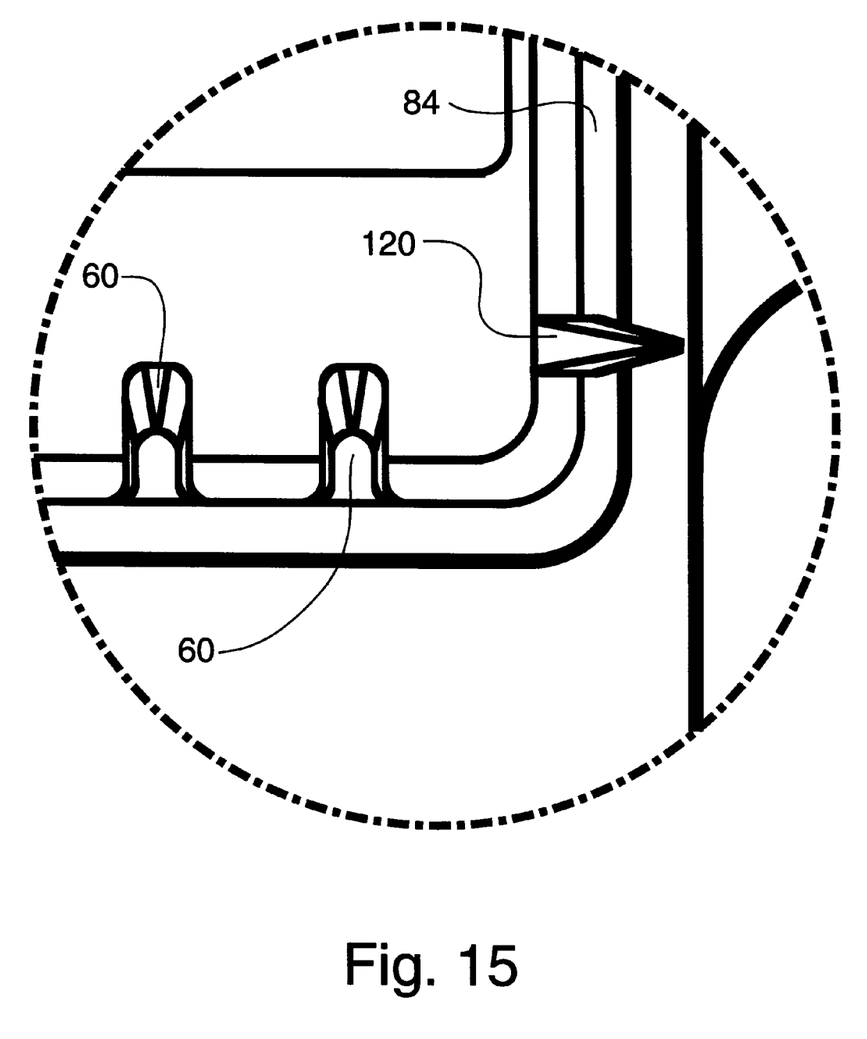
FIG. 15 is an enlarged view of one portion of the tray in FIG. 14.

FIGS. 14 and 15 show an alternative embodiment of the tray 10, having fracture slots or ridges 120. In the embodiment as depicted, four fracture slots 120 are disposed in a proximate position to the corners of open top cavity 16. Of course, any number of fracture slots 120 can be disposed upon tray 10. Fracture slots 120 provide for the material to "break" in the corners during this flexing. This breaking will result in the four sides 11, 12 13 and 14 being independent of one another during the flexing and will provide release of any physical or mechanical interaction of the set dental stone and the tray. This independent flexing of the sides provides uniformity of the release, eliminating difficulty in flexing the otherwise rigid corners of open top cavity 16.

It will be appreciated that use of tray 10 according to the invention and as described above, is useful for creating a positive replica of a patient's teeth. Individual sections of the replica can be removed from the model and the tray 10 through open top cavity 16, and then be easily, quickly and precisely returned to its original position. The tray 10 is particularly suited for a one-pour replicating technique, and provide accurate indexing without the use of pins. While particularly suited for dental applications, it will also be appreciated that the tray 10 of the present invention has application to refractory die making and the like.

It is apparent therefore, that the modeling device as described above carries out and accomplishes the objects of the present invention. While the principles of the embodiments of the invention have been shown in the drawings and described above, those skilled in the art may make modifications of structure, arrangement, proportions, elements, materials and components used in the practice of the invention which are particularly adapted for specific environments and operating requirements without departing from those principles, and all of which are within the scope of the invention.

I claim:

1. A dental stone casting mold device for use with a hardenable stone material, comprising:

associated first and second side wall means, first and second end wall means and floor means forming an open top cavity means;

each said first and second side wall means and said first and second end wall means extending from said floor means in a lateral direction, such that each has a portion proximate to said floor means and a portion distal thereto;

at least one slot means in said floor means for removably receiving a stone retaining spine means;

said first and second side wall means being in a spaced and opposing relation to each other;

each of said first and second side wall means carrying a plurality of spaced indexing ribs, said indexing ribs extending in a direction substantially parallel to said lateral direction extension of its associated side wall, such that each said indexing rib has a linear dimension;

at least one indexing rib of said first side wall having a said linear dimension greater than the said linear dimension of at least one said indexing rib of said second side wall.

2. A dental stone casting mold device as in claim 1, wherein said plurality of indexing ribs of said first side wall are placed in a staggered opposing relation to said plurality of indexing ribs of said second side wall.

3. A dental stone casting mold device as in claim 1, wherein each said indexing rib has a portion proximate to said floor means and a portion distal thereto; said ribs tapering outwardly from said distal portion to said proximate portion.

4. A dental stone casting mold device as in claim 1, further comprising in combination, a spine means having a slot retaining portion and a stone material retaining portion.

5. A dental stone casting mold device as in claim 4, wherein said slot retaining portion comprises resilient and opposing retention member means configured to be cooperatively and removably received within and through said slot means, such that said retention member means are deformable when received within said slot means, and resiliently expandable after passage through said slot means.

6. A dental stone casting mold device as in claim 5, further comprising a flange means positioned between said slot retaining portion and said stone material retaining portion, such that said flange means limits the distance to which said retention member means can be received through said slot means.

7. A dental stone casting mold device as in claim 5, further comprising a downwardly extending skirt extending laterally from said floor means in a direction other than that of said first and second side wall means, such that an open bottom cavity means is formed opposite that of said open top cavity means.

8. A dental stone casting mold device as in claim 4, wherein said stone material retaining portion includes a linearly extending bead means, such that the stone material is formed around said bead.

9. A dental stone casting mold device as in claim 8, wherein said bead is bulbous in cross section.

10. A dental stone casting mold device as in claim 8, wherein said bead is provided with a plurality of groove means, such that said groove means substantially prevent laterally movement of stone material hardened about said bead.

11. A dental stone casting mold device for use with a hardenable stone material, comprising:

associated first and second side wall means, first and second end wall means and floor means forming an open top cavity means;

each said first and second side wall means and said first and second end wall means extending from said floor means in a lateral direction, such that each has a portion proximate to said floor means and a portion distal thereto;

at least one slot means in said floor means for removably receiving a stone retaining spine means;

said first and second side wall means being in a spaced and opposing relation to each other;

each of said first and second side wall means carrying a plurality of spaced indexing ribs, said indexing ribs extending in a direction substantially parallel to said lateral direction extension of its associated side wall, such that each said indexing rib has a linear dimension;

at least one indexing rib of said first side wall having a said linear dimension greater than the said linear dimension of at least one said indexing rib of said second side wall;

each said distal end of said first and second side walls having integrally associated lateral extensions therefrom;

each said distal end of said first and second wall means having a linearly extending, raised fracture lip; and, said first end wall means carrying an integrally associated articulator attachment means; such that a pair of the dental stone casting mold devices can be removably positioned in a spaced and opposing relation by attachment of said articulator through said articulator attachment means.

12. A dental stone casting mold device as in claim 11, wherein said plurality of indexing ribs of said first side wall are placed in a staggered opposing relation to said plurality of indexing ribs of said second side wall.

13. A dental stone casting mold device as in claim 11, wherein each said indexing rib has a portion proximate to said floor means and a portion distal thereto; said ribs tapering outwardly from said distal portion to said proximate portion.

14. A dental stone casting mold device as in claim 11, further comprising in combination, a spine means having a slot retaining portion and a stone material retaining portion.

15. A dental stone casting mold device as in claim 14, wherein said slot retaining portion comprises resilient and opposing retention member means configured to be cooperatively and removably received within and through said slot means, such that said retention member means are deformable when received within said slot means, and resiliently expandable after passage through said slot means.

16. A dental stone casting mold device as in claim 15, further comprising a flange, means positioned between said slot retaining portion and said stone material retaining portion, such that said flange means limits the distance to which said retention member means can be received through said slot means.

17. A dental stone casting mold device as in claim 15, further comprising a downwardly extending skirt extending laterally from said floor means in a direction other than that of said first and second side wall means, such that an open bottom cavity means is formed opposite that of said open top cavity means.

18. A dental stone casting mold device as in claim 14, wherein said stone material retaining portion includes a linearly extending bead means, such that the stone material is formed around said bead.

19. A dental stone casting mold device as in claim 18, wherein said bead is bulbous in cross section.

20. A dental stone casting mold device as in claim 18, wherein said bead is provided with a plurality of groove means, such that said groove means substantially prevent laterally movement of stone material hardened about said bead.

* * * * *